United States Patent
Kim

(10) Patent No.: US 10,669,055 B2
(45) Date of Patent: Jun. 2, 2020

(54) CONTROL APPARATUS

(71) Applicant: JVM Co., Ltd., Daegu (KR)

(72) Inventor: Jun-ho Kim, Daegu (KR)

(73) Assignee: JVM CO., LTD., Daegu (KR)

( * ) Notice: Subject to any disclaimer, the term of this patent is extended or adjusted under 35 U.S.C. 154(b) by 422 days.

(21) Appl. No.: 15/604,170

(22) Filed: May 24, 2017

(65) Prior Publication Data

US 2017/0341794 A1 Nov. 30, 2017

(30) Foreign Application Priority Data

May 26, 2016 (KR) .................. 10-2016-0065014

(51) Int. Cl.
| | | |
|---|---|---|
| *B65B 57/00* | (2006.01) | |
| *B65B 57/08* | (2006.01) | |
| *A61J 7/00* | (2006.01) | |
| *B65B 57/10* | (2006.01) | |
| *G07F 17/00* | (2006.01) | |
| *B65B 57/02* | (2006.01) | |
| *G07F 11/44* | (2006.01) | |

(Continued)

(52) U.S. Cl.
CPC ............ *B65B 57/08* (2013.01); *A61J 7/0084* (2013.01); *B65B 1/04* (2013.01); *B65B 5/103* (2013.01); *B65B 35/26* (2013.01); *B65B 57/00* (2013.01); *B65B 57/02* (2013.01); *B65B 57/04* (2013.01); *B65B 57/10* (2013.01); *B65B 57/12* (2013.01); *B65B 57/18* (2013.01); *G07F 11/44* (2013.01); *G07F 11/70* (2013.01); *G07F 17/0092* (2013.01); *B65B 2210/04* (2013.01); *G16H 20/13* (2018.01)

(58) Field of Classification Search
CPC ..... G07F 17/0092; B65B 57/08; B65B 57/04; B65B 57/10; G01N 21/9508
See application file for complete search history.

(56) References Cited

U.S. PATENT DOCUMENTS 6,324,253 B1 * 11/2001 Yuyama ................. G01N 23/04
209/589
7,536,938 B2 * 5/2009 Kim ......................... B26D 7/32
83/209

(Continued)

FOREIGN PATENT DOCUMENTS

EP           2702978 A1    3/2014
KR   10-2012-0102875 A    9/2012

(Continued)

OTHER PUBLICATIONS

Extended European Search Report dated Oct. 26, 2017 for European application No. 17172904.9.

*Primary Examiner* — Timothy R Waggoner
(74) *Attorney, Agent, or Firm* — Ohlandt, Greeley, Ruggiero & Perle, L.L.P.

(57) ABSTRACT

A control apparatus is provided. The control apparatus includes: a packaged medicine preparation unit discharging a bundle of packaged medicines in which a large amount of medicines are prepared by one capsule in a single dose to perform a post-process on the bundle of packaged medicines for a specific purpose based on a medicine dispensing request; and a post-processing unit introduced with the bundle of packaged medicines discharged from the packaged medicine preparation unit to perform the post-process thereon.

14 Claims, 16 Drawing Sheets

(51) Int. Cl.
*B65B 57/18* (2006.01)
*G07F 11/70* (2006.01)
*B65B 1/04* (2006.01)
*B65B 5/10* (2006.01)
*B65B 35/26* (2006.01)
*B65B 57/04* (2006.01)
*B65B 57/12* (2006.01)
*G16H 20/13* (2018.01)

(56) References Cited

U.S. PATENT DOCUMENTS

| | | |
|---|---|---|
| 9,272,796 B1* | 3/2016 | Chudy .................... B65B 5/103 |
| 2002/0014055 A1 | 2/2002 | Iwasa |
| 2006/0213816 A1* | 9/2006 | Jorritsma ........... G01N 21/9508 |
| | | 209/576 |
| 2006/0230710 A1 | 10/2006 | Ishiwatari |
| 2007/0000805 A1 | 1/2007 | Van Den Brink |
| 2012/0290129 A1* | 11/2012 | Luciano, Jr. ........... B65D 75/42 |
| | | 700/244 |
| 2012/0330684 A1 | 12/2012 | Jacobs |
| 2013/0318931 A1* | 12/2013 | Holmes .................... B65B 1/02 |
| | | 53/562 |
| 2013/0342676 A1* | 12/2013 | Amano .................... H04N 7/18 |
| | | 348/86 |
| 2014/0236349 A1 | 8/2014 | Bae |
| 2016/0379361 A1 | 12/2016 | Kim |

FOREIGN PATENT DOCUMENTS

| | | |
|---|---|---|
| KR | 10-2014-0105625 A | 9/2014 |
| KR | 10-2017-0001467 A | 1/2017 |

* cited by examiner

310

CONTROL APPARATUS

CROSS-REFERENCE TO RELATED APPLICATIONS

This application claims priority from Korean Patent Application No. 10-2016-0065014, filed on May 26, 2016 in the Korean Intellectual Property Office the disclosure of which is incorporated herein by reference in its entirety.

BACKGROUND OF THE INVENTION

Field of the Invention

Apparatuses and method consistent with the present disclosure relate to a control apparatus, and more particularly, to a control apparatus for allowing a bundle of packaged medicines in which a large amount of medicines are packaged by one capsule in a single dose to be smoothly transferred to a post-process for a specific purpose.

Description of the Related Art

According to the related art, a medicine automatic packaging machine of receiving medicines from a plurality of cassette apparatuses in which each kind of medicines such as tablets, capsules or the like are accommodated and continuously packaging the medicines by one capsule in a single dose has been developed and used.

As the medicine automatic packaging machine according to the related art, a medicine automatic packaging machine including a plurality of cassette apparatuses disposed at an upper portion of a body and accommodating medicines such as tablets, capsules, or the like, having various sizes and shapes therein, a hopper disposed at a lower portion of the body and collecting medicines discharged and dropping from the cassette apparatuses, a printing apparatus printing various information on a surface of packing paper packaging the medicines, and a packaging apparatus packaging the medicines collected by the hopper using the packing paper has been used.

The medicines packaged by one capsule by the medicine automatic packaging machine as described above suffer from a post-process for a specific purpose. For example, the post-process for the specific purpose may be an inspection process.

That is, since several ten to several hundred kinds of medicines are accommodated in the respective cassette apparatuses of the medicine automatic packaging machine and there is a risk that a medicine accident will occur in the case in which inaccurate medicines are packaged, it should be necessarily inspected whether medicines are accurately packaged in packages in which the medicines are packaged.

In addition, it should be necessarily inspected whether or not the medicines have been damaged due to a collision with a surface of the hopper, or the like, when the medicines are discharged and drop or whether or not medicines more than or less than a defined number of medicines have been packaged due to an error in a packaging operation.

Here, it is necessary to transfer the medicines packaged by one capsule to a specific device for the above-described post-process. Conventionally, there has been a problem that the packaged medicines are cut during the transfer of the packaged medicines due to various problems.

Therefore, researches to facilitate the transfer of the packaged medicines are urgently needed.

SUMMARY OF THE INVENTION

Exemplary embodiments of the present invention overcome the above disadvantages and other disadvantages not described above. Also, the present invention is not required to overcome the disadvantages described above, and an exemplary embodiment of the present invention may not overcome any of the problems described above.

The present disclosure provides a control apparatus for preventing a bundle of packaged medicines from being cut abnormally by allowing the bundle of medicines packaged by one capsule in a single dose to be smoothly transferred to a post-process for a specific purpose.

According to an aspect of the present disclosure, a control apparatus includes: a packaged medicine preparation unit discharging a bundle of packaged medicines in which a large amount of medicines are prepared by one capsule in a single dose to perform a post-process on the bundle of packaged medicines for a specific purpose based on a medicine dispensing request; and a post-processing unit introduced with the bundle of packaged medicines discharged from the packaged medicine preparation unit to perform the post-process thereon, in which the packaged medicine preparation unit may include a discharge unit moving a position of the bundle of packaged medicines prepared by one capsule in the single dose to perform the post-process thereon, and the post-processing unit may include a transfer unit moving the position of the bundle of packaged medicines to perform the post-process thereon if the bundle of packaged medicines discharged from the discharge unit is introduced thereinto, and in which the control apparatus may further include a control unit allowing a transfer speed of the bundle of packaged medicines by the transfer unit to be associated with a discharge speed of the bundle of packaged medicines by the discharge unit and controlling at least one of the transfer unit and the discharge unit to allow the post-processing unit to perform the post-process thereon without damaging the bundle of packaged medicines.

The control unit may acquire at least one of first information associated with the discharge speed of the bundle of packaged medicines by the discharge unit and second information associated with the transfer speed of the bundle of packaged medicines by the transfer unit and control at least one of the transfer unit and the discharge unit based on the acquired information.

The control unit may acquire first information associated with the discharge speed of the bundle of packaged medicines by the discharge unit and control the transfer unit based on the acquired first information so that the transfer unit controls the transfer speed of the bundle of packaged medicines.

The control unit may acquire first information associated with the discharge speed of the bundle of packaged medicines by the discharge unit and control the transfer unit based on the acquired first information so that the transfer speed of the bundle of packaged medicines by the transfer unit is synchronized with the discharge speed of the bundle of packaged medicines by the discharge unit.

The control unit may acquire first information associated with the discharge speed of the bundle of packaged medicines by the discharge unit and control the transfer unit based on the acquired first information so that the transfer speed of the bundle of packaged medicines by the transfer unit is equal to the discharge speed of the bundle of packaged medicines by the discharge unit.

If the control unit controls at least one of the transfer unit and the discharge unit and acquires third information associated with the bundle of packaged medicines existing between the transfer unit and the discharge unit, the control unit may control the transfer unit based on the acquired third information so that the transfer unit controls the transfer speed of the bundle of packaged medicines.

The control unit may stop the transfer unit based on the acquired third information.

If the control unit stops the transfer unit and then stops acquiring the third information, the control unit may control the transfer unit so that the transfer unit transfers the bundle of packaged medicines.

The post-processing unit may further include a packaged medicine inspecting unit inspecting whether or not any packaged medicine of the bundle of packaged medicines introduced thereinto corresponds to the medicine dispensing request.

The packaged medicine preparation unit may further include a first detection unit for acquiring a discharge speed of the bundle of packaged medicines by the discharge unit and the control unit may acquire a detected result by the first detection unit to control the transfer unit so that the transfer unit controls the transfer speed of the bundle of packaged medicines.

The packaged medicine inspecting unit may include a second detection unit detecting whether the bundle of packaged medicines existing between the transfer unit and the discharge unit exists in a predetermined space between the transfer unit and the discharge unit.

The control unit may control at least one of the transfer unit and the discharge unit and control the transfer unit so that the transfer unit controls the transfer speed of the bundle of packaged medicines if a detected result by the second detection unit is acquired.

The control unit may stop the transfer unit if the detected result by the second detection unit is acquired.

If the transfer unit stops and then the information acquired from the second detection unit is lost, the control unit may control the transfer unit so that the transfer unit transfers the bundle of packaged medicines.

The packaged medicine inspecting unit may include an inflow guide unit that is disposed on an upstream side of the transfer unit to provide a predetermined external force to the bundle of packaged medicines so that the bundle of packaged medicines discharged from the discharge unit is introduced thereinto to be transferred to the transfer unit.

The inflow guide unit may include a state change means that is formed in a curved surface so that the bundle of packaged medicines discharged in a first state by the discharge unit moves to the transfer unit in a second state different from the first state.

The inflow guide unit may allow the bundle of packaged medicines to be introduced in which the bundle of packaged medicines is discharged from the discharge unit, and transfer the introduced bundle of packaged medicines to the transfer unit in a state different from the state in which the bundle of packaged medicines is discharged.

The packaged medicine inspecting unit may further include a third detection unit detecting whether the bundle of packaged medicines introduced thereinto by the inflow guide unit is introduced into the transfer unit, and the control unit may control the inflow guide unit to reduce the predetermined external force if the detected result by the third detection unit is acquired.

The inflow guide unit may include a first inflow conveyor belt and a second inflow conveyor belt each contacting an upper surface and a lower surface of the bundle of packaged medicines, and the control unit may move a position of at least one of the first inflow conveyor belt and the second inflow conveyor belt to reduce the predetermined external force if the detected result by the third detection unit is acquired.

The packaged medicine inspecting unit may further include a tension maintaining means pressing the bundle of packaged medicines to maintain a tension of the bundle of packaged medicines introduced into the transfer unit if the bundle of packaged medicines introduced thereinto by the inflow guide unit is introduced into the transfer unit.

The packaged medicine inspecting unit may include a photographing unit configured to photograph an arbitrary packaged medicine of the bundle of packaged medicines, and a light source unit configured to provide light for photographing of the photographing unit, and the control unit may read a state of the arbitrary packaged medicine through an image photographed by the photographing unit.

At least one of the photographing unit and the light source unit of the control apparatus may include a polarizing unit that makes polarization incident on the photographing unit to ensure accuracy of the image photographed by the photographing unit.

According to the control apparatus of the present disclosure, it is possible to previously prevent a bundle of packaged medicines from being cut abnormally by smoothly transferring the bundle of packaged medicines, in which a large amount of medicines are packaged by one capsule in a single dose, to the post-process for the specific purpose.

BRIEF DESCRIPTION OF THE DRAWING FIGURES

The above and/or other aspects of the present invention will be more apparent by describing certain exemplary embodiments of the present invention with reference to the accompanying drawings, in which:

FIGS. 10 to 12 are internal configuration diagrams for explaining an inflow guide unit provided to a packaged medicine inspecting unit according to the exemplary embodiment of the present disclosure; and.

DETAILED DESCRIPTION OF THE EXEMPLARY EMBODIMENTS

Figure 1:
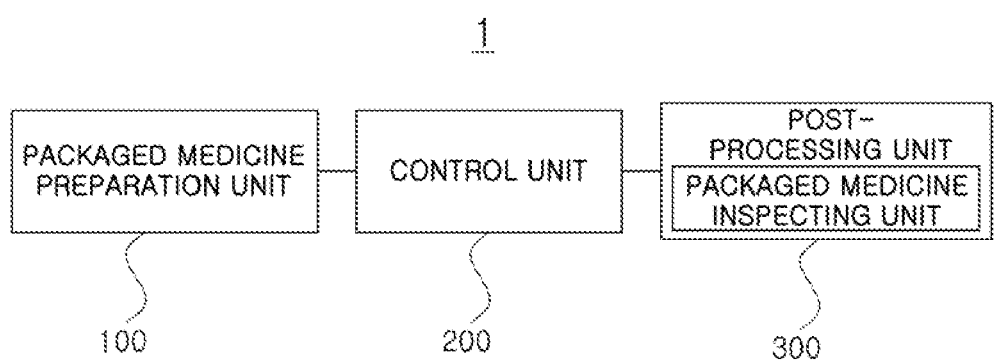
FIGS. 1 and 2 are block configuration diagrams for explaining a control apparatus according to an exemplary embodiment of the present disclosure.

Exemplary embodiments of the present disclosure will now be described in detail with reference to the accompanying drawings. However, it should be noted that the spirit of the present disclosure is not limited to the exemplary embodiments set forth herein and those skilled in the art and understanding the present disclosure can easily accomplish retrogressive disclosures or other exemplary embodiments included in the spirit of the present disclosure by the addition, modification, and removal of components within the same spirit, but those are construed as being included in the spirit of the present disclosure.

Further, like reference numerals will be used to designate like components having similar functions throughout the drawings within the scope of the present disclosure.

1. Control Apparatus

Figure 2:
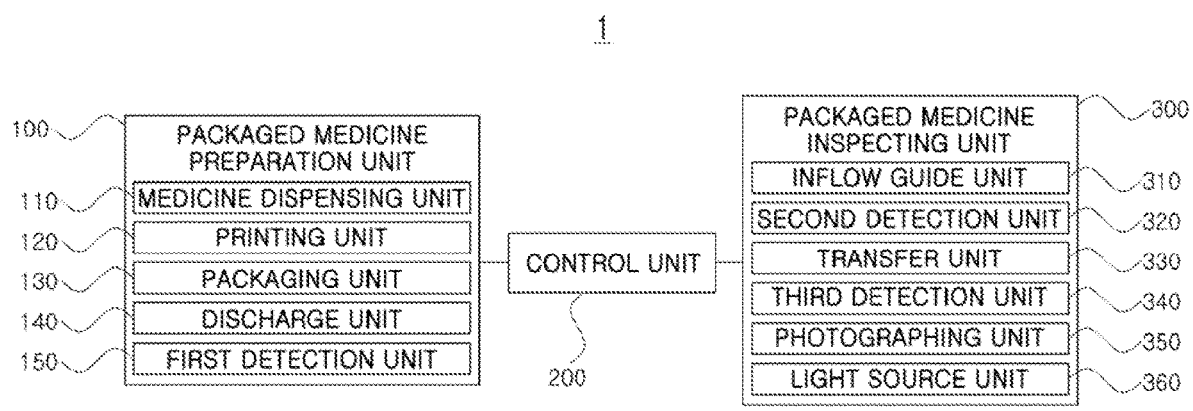
Figure 3:
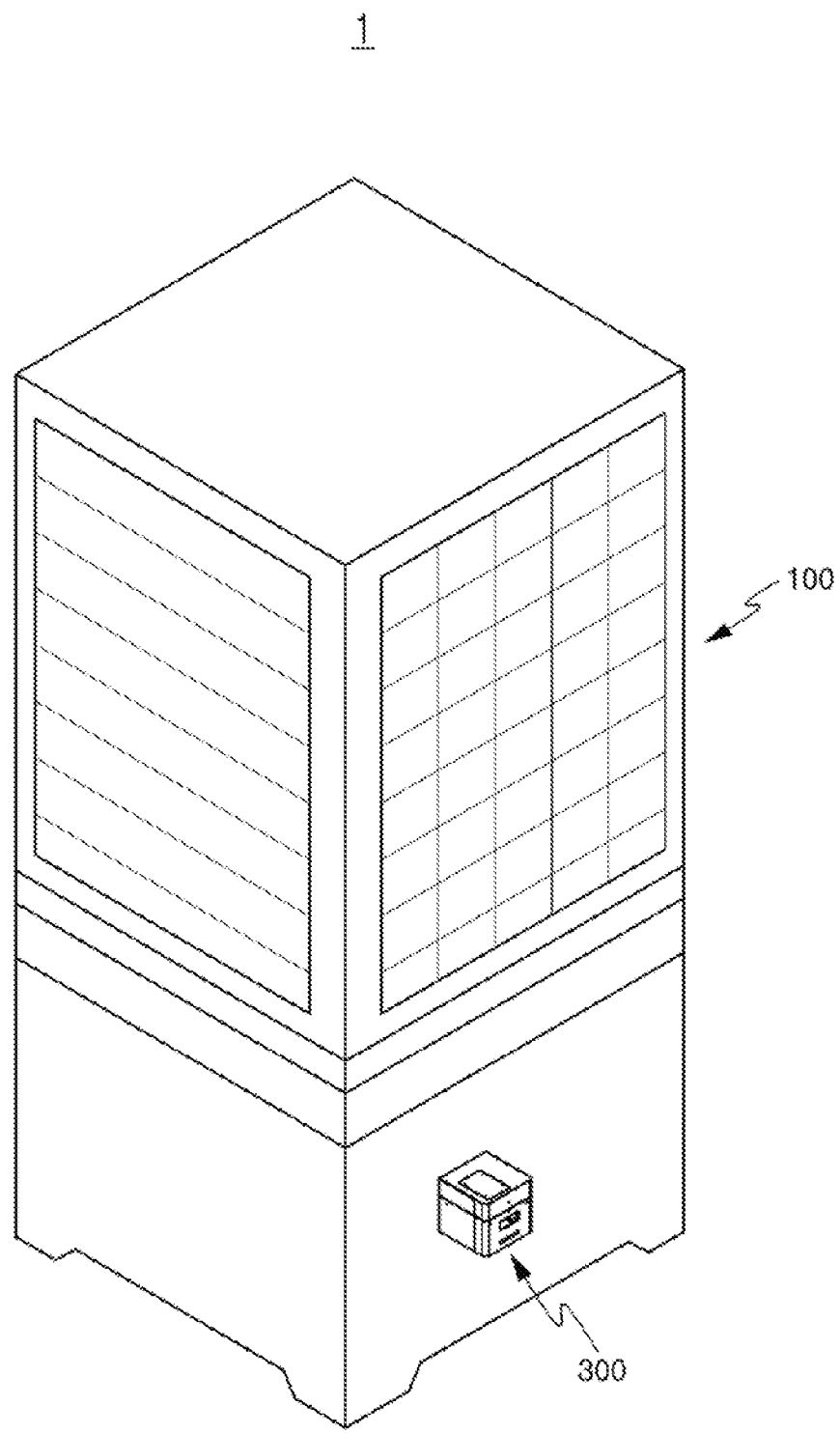
FIG. 3 is a schematic perspective view showing the control apparatus according to the exemplary embodiment of the present disclosure.

FIGS. 1 and 2 are block configuration diagrams for explaining a control apparatus according to an exemplary embodiment of the present disclosure and FIG. 3 is a schematic perspective view showing the control apparatus according to the exemplary embodiment of the present disclosure.

Referring to FIGS. 1 to 3, a control apparatus 1 according to an exemplary embodiment of the present disclosure is to prevent a bundle of medicines packaged by one capsule in a single dose from being cut abnormally by allowing the bundle of medicines to be smoothly transferred to a post-process for a specific purpose and may include a packaged medicine preparation unit 100, a post-processing unit 300, and a control unit 200.

The packaged medicine preparation unit 100 may be an apparatus that prepares a large amount of medicines by one capsule in a single dose based on a medicine dispensing request (e.g., patient prescription data, etc.) and discharges a bundle of packaged medicines to perform the post-process for a specific purpose.

In other words, the packaged medicine preparation unit 100 may be an apparatus for producing packaged medicines by automatically packaging medicines dispensed from a medicine dispensing unit 110, which has accommodated medicines, with packing paper based on the medicine dispensing request.

For the implementation of the above-mentioned functions, the packaged medicine preparation unit 100 may include a packaging unit 130 for packaging the medicines dispensed from the medicine dispensing unit 110 with the packing paper and a discharge unit 140 for discharging the bundle of packaged medicines produced by the packaging unit 130 and may further include a printing unit 120 for printing information on the packing paper.

Here, the medicine dispensing request may include prescription data such as patient's personal information, information on a type and quantity of medicines to be taken, information on taking medicine duration, and disease information.

The packaged medicine preparation unit 100 allows medicines to be dispensed from the corresponding medicine dispensing unit 110 based on the medicine dispensing request, and the dispensed medicines to be packaged with the packing paper on which the information is printed by the printing unit 120, and a bundle of packaged medicines to be discharged to the outside through the discharge unit 140.

The post-processing unit 300 is a component for receiving a bundle of packaged medicines discharged from the packaged medicine preparation unit 100 and performing a post-process on the bundle of packaged medicines and may be, for example, a packaged medicine inspecting unit 300 as shown in FIG. 2.

The packaged medicine inspecting unit 300 may be an apparatus that inspects whether any packaged medicines included in a bundle of packaged medicines discharged from the packaged medicine preparation unit 100 correspond to the medicine dispensing request, that is, patient's prescription data (preparation information), or the like.

Here, the packaged medicine inspecting unit 300 may inspect any packaged medicines included in a bundle of packaged medicines by a process of comparing the patient's prescription data and medicine information stored in a medicine image storage unit (not shown) with a medicine image photographed by a photographing unit 350 that is a kind of camera.

The control unit 200 may be a component for controlling a discharge speed of a bundle of packaged medicines by the packaged medicine preparation unit 100 and a transfer speed of the bundle of packaged medicines by the packaged medicine inspecting unit 300.

Hereinafter, in describing the control apparatus 1 according to the exemplary embodiment of the present disclosure, an operation principle or the like of each of the packaged medicine preparation unit 100 and the post-processing unit 300 will first be described and a control process by the control unit 200 will be described in detail.

2. Packaged Medicine Preparation Unit

Figure 4:
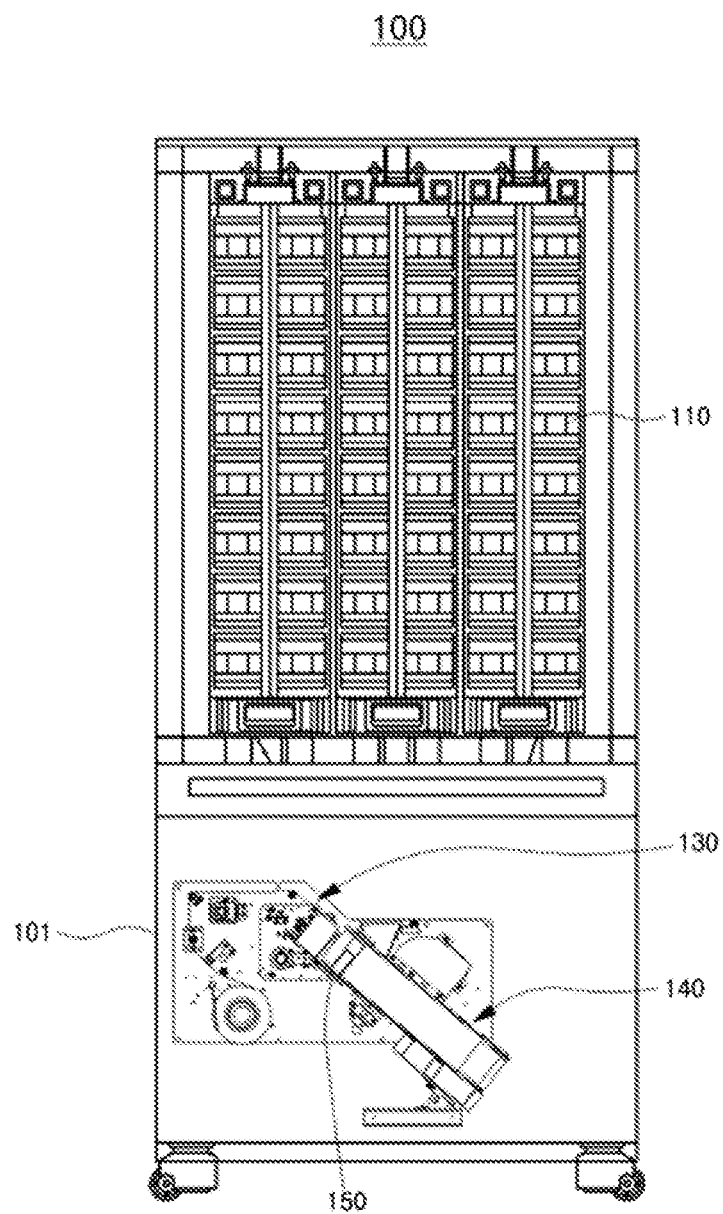
FIG. 4 is an internal configuration diagram for explaining a packaged medicine preparation unit provided in the control apparatus according to the exemplary embodiment of the present disclosure.
Figure 5:
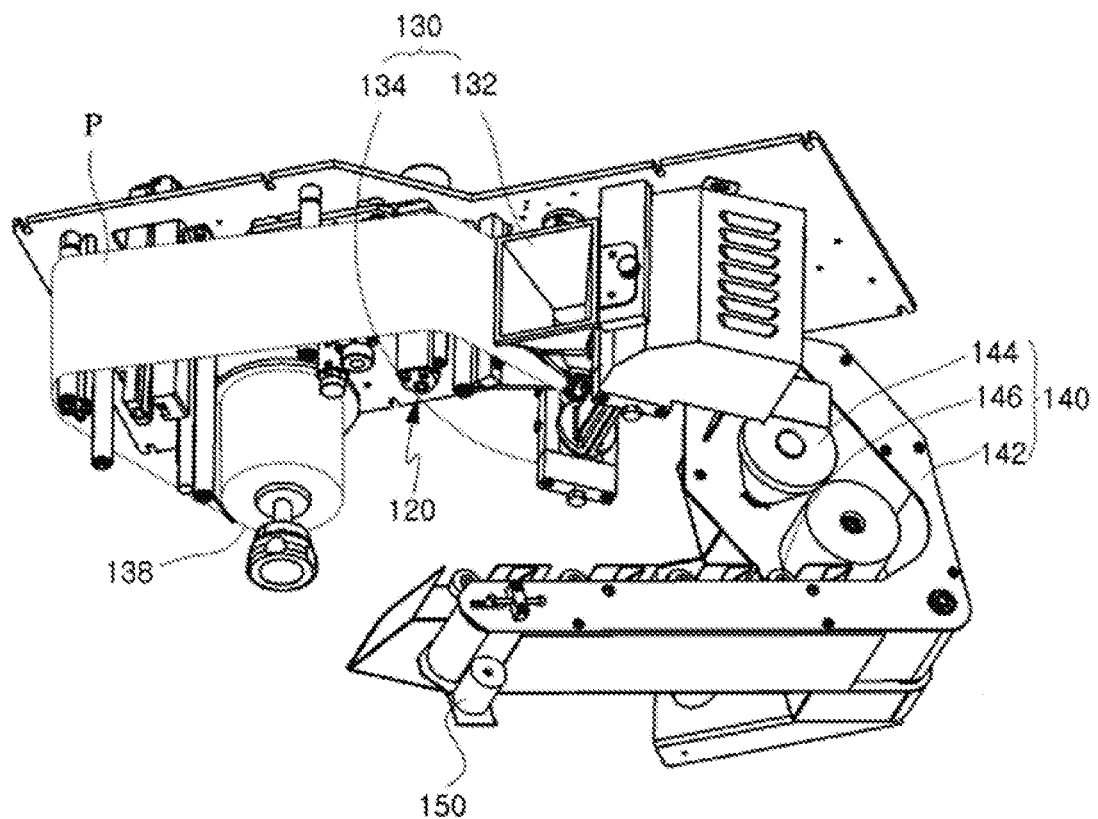
FIG. 5 is a schematic perspective view showing a discharge unit or the like provided in the packaged medicine preparation unit shown in FIG. 4.

FIG. 4 is an internal configuration diagram for explaining a packaged medicine preparation unit provided in the control apparatus according to the exemplary embodiment of the present disclosure and FIG. 5 is a schematic perspective view showing a discharge unit or the like provided in the packaged medicine preparation unit shown in FIG. 4.

Referring to FIGS. 4 and 5, the packaged medicine preparation unit 100 according to the exemplary embodiment of the present disclosure may include the packaging unit 130 that is installed inside a main body unit 101 and supplied with medicines from a plurality of medicine dispensing units 110 positioned on an upper side thereof and packages the medicines with packing paper P on which information is printed by the printing unit 120 and the discharge unit 140 that discharges a bundle of medicines packaged by the packaging unit 130.

The packaging unit 130 may include a hopper unit 132 that collects medicines supplied from the medicine dispensing unit 110 to one point, a packing paper winding roll 138 supplying packing paper on which the medicines collected through the hopper unit 132 are seated, and a sealing unit 134 that seals the packing paper P on which medicines are seated and packages the medicines.

Specifically, the hopper unit 132 is positioned under the medicine dispensing unit 110, the packing paper P wound by the packing paper winding roll 138 is positioned under the hopper unit 132, and one side of the packing paper P is provided with the sealing unit 134 to seal medicines discharged from the hopper unit 132 to the packing paper P when the medicines are enclosed with the packing paper P.

The discharge unit 140 may be a component for moving a position of a bundle of medicines packaged by one capsule in a single dose using the packaging unit 130 and performing the post-process on the bundle of medicines using the post-processing unit 300.

The discharge unit 140 may include a discharge conveyor belt 142 that transfers a bundle of packaged medicines sealed by the sealing unit 134 to the outlet, a first transfer guide roller 144 that guides a transfer of the bundle of packaged medicines, a second transfer guide roller 146 that is installed to contact an upper surface of the bundle of packaged medicines seated on the discharge conveyor belt 142 to guide the transfer of the bundle of packaged medicines, or the like.

In this configuration, the discharge conveyor belt 142 is formed to be obliquely inclined so that if the bundle of medicines packaged by the sealing unit 134 of the packaging unit 130 is input to be seated on an upper surface thereof while being discharged downward by a self weight of the medicines, one side thereof is adjacent to the sealing unit 134 and the other side thereof is bent toward a side opposite thereto, that is, upwardly to transfer the bundle of medicines to an outlet positioned at the upper side thereof.

The discharge conveyor belt 142 obliquely bent is positioned on a front side of the packaging unit 130 so that the bundle of packaged medicines seated on the discharge conveyor belt 142 is guided by the first transfer guide roller 144 and the second transfer guide roller 146 to be transferred along the bent discharge conveyor belt 142 and to be discharged to the outlet.

Meanwhile, the packaged medicine preparation unit 100 may include a first detection unit 150 that acquires the discharge speed of the bundle of packaged medicines by the discharge unit 140.

As the first detection unit 150, any means (for example, optical sensor, ultrasonic sensor, tact switch, etc.) may be applied as long as it may sense the discharge speed of the bundle of packaged medicines. For example, the first detection unit 150 may be an encoder that is disposed to contact the discharge conveyor belt 142 of the discharge unit 140.

The encoder may detect the discharge speed of the bundle of packaged medicines because RPM is changed depending on a moving speed of the discharge conveyor belt 142, and the detected result is transmitted to the controller 200.

The control unit 200 may control at least one of the discharge unit 140 and a transfer unit 330 of the packaged medicine inspecting unit 300 based on the result detected by the first detection unit 150, which will be described below.

3. Post-Processing Unit

Figure 6:
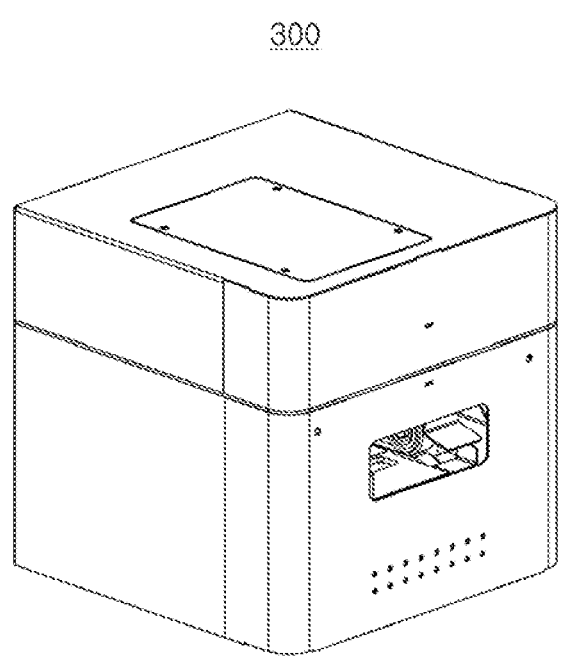
FIG. 6 is a schematic perspective view showing a post-processing unit, that is, a packaged medicine inspecting unit that is provided in the control apparatus according to the exemplary embodiment of the present disclosure.
Figure 7:
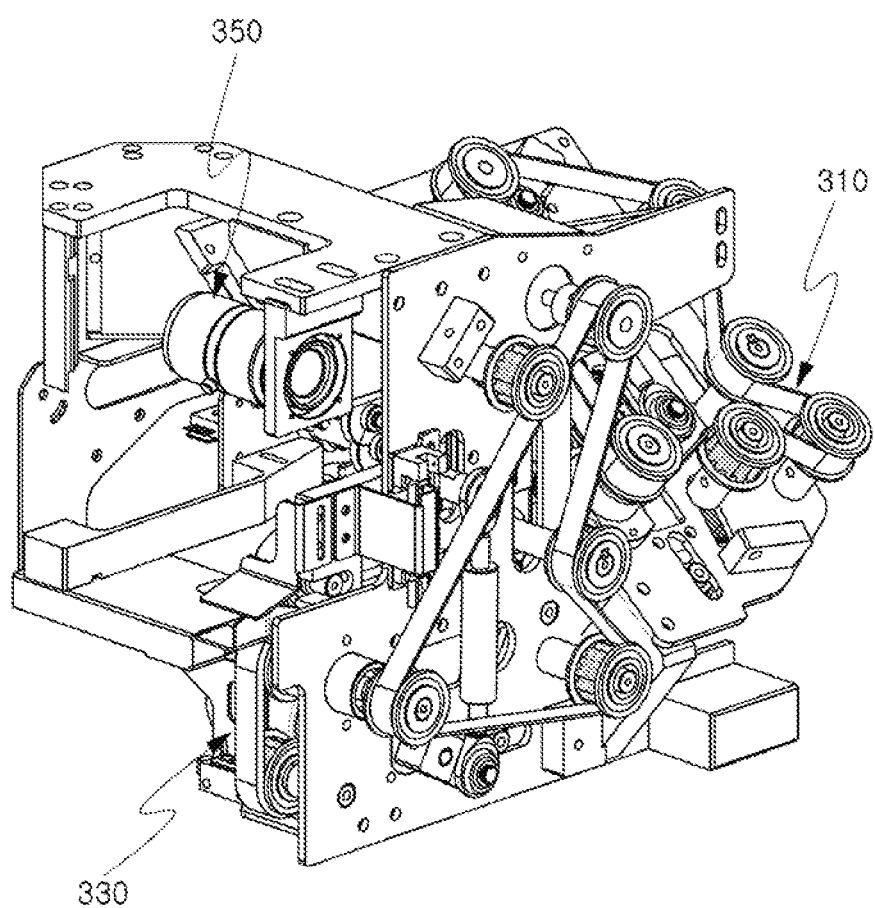
FIGS. 7 to 9 are internal configuration diagrams for explaining the packaged medicine inspecting unit according to the exemplary embodiment of the present disclosure.
Figure 8:
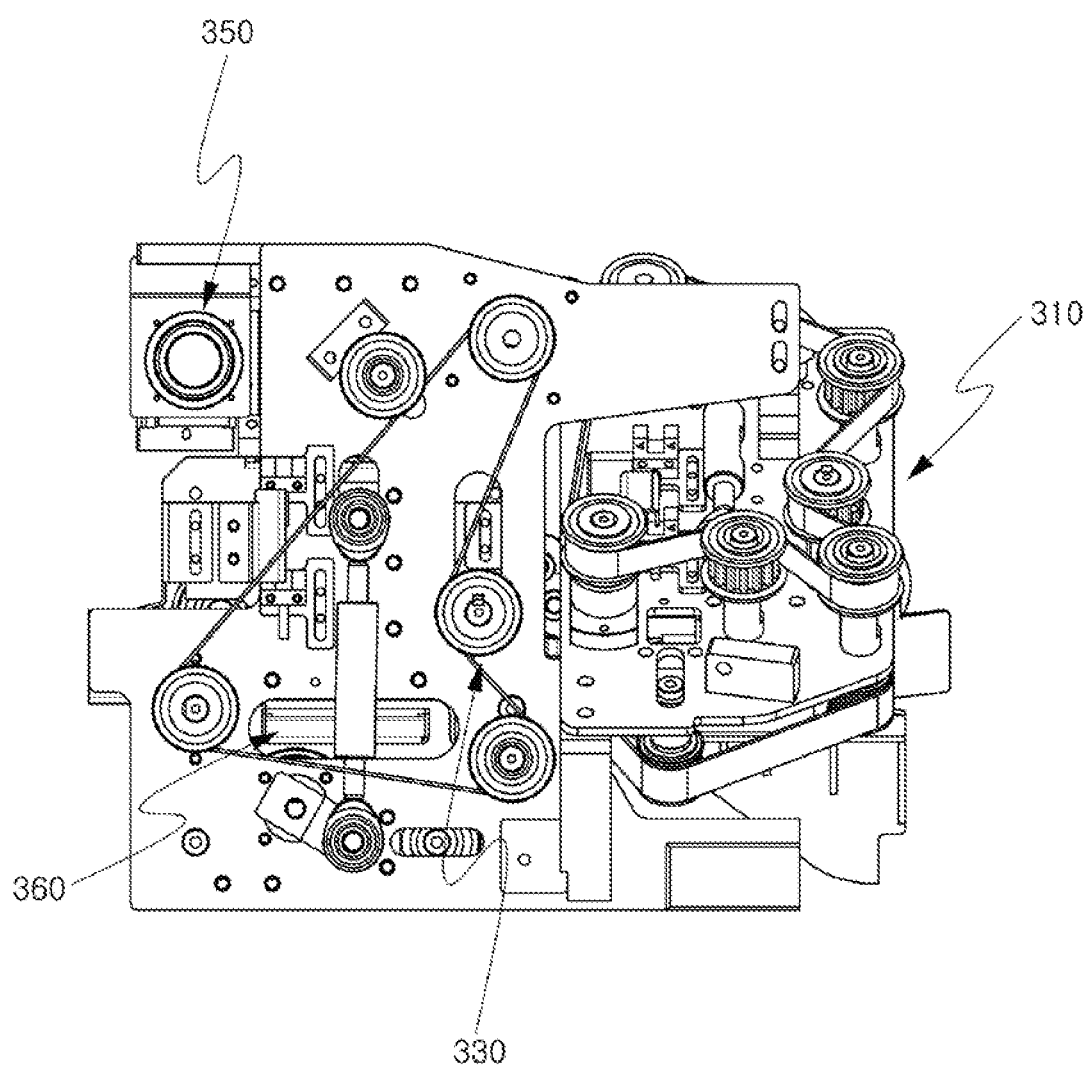
Figure 9:
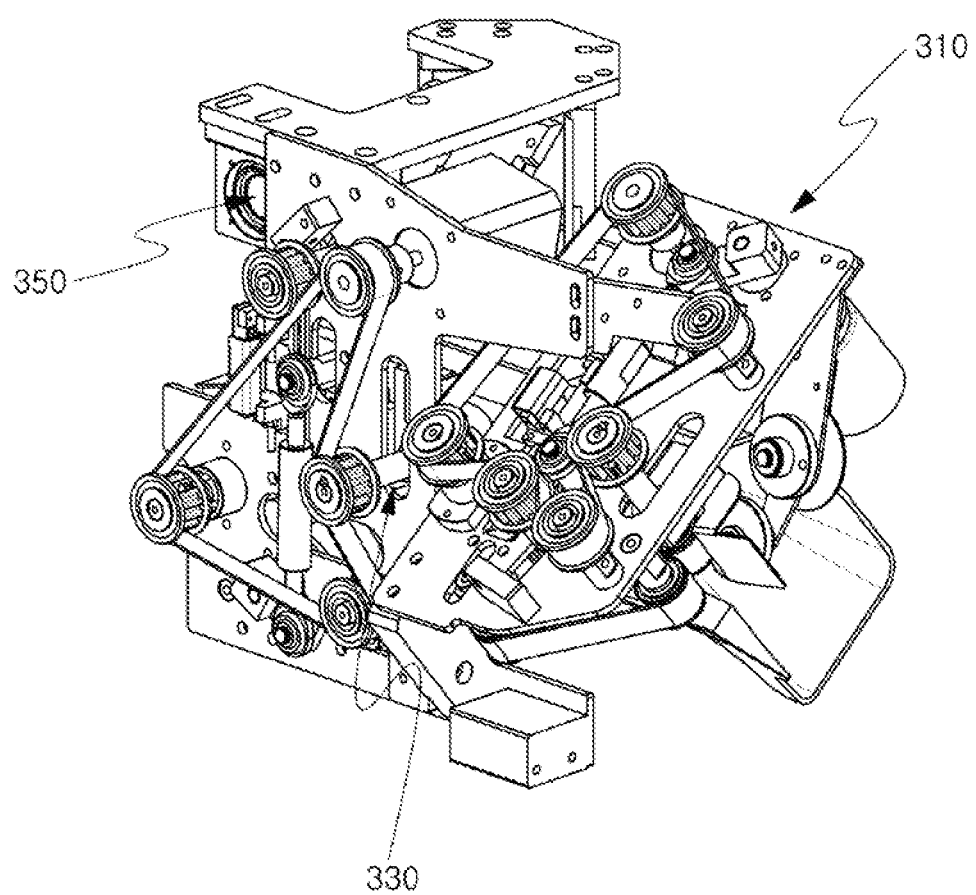

FIG. 6 is a schematic perspective view showing a post-processing unit, that is, a packaged medicine inspecting unit that is provided in the control apparatus according to the exemplary embodiment of the present disclosure and FIGS. 7 to 9 are internal configuration diagrams for explaining the packaged medicine inspecting unit according to the exemplary embodiment of the present disclosure.

Referring to FIGS. 6 to 9, the packaged medicine inspecting unit 300, which is the post-processing unit 300, may include the inflow guide unit 310, the transfer unit 330, the photographing unit 350, a light source unit 360, or the like.

The packaged medicine inspecting unit 300 may inspect any packaged medicines included in a bundle of packaged medicines by the process of comparing the patient's prescription data and the medicine information stored in the medicine image storage unit with the medicine image photographed by the photographing unit 350 that is a kind of camera.

Specifically, the packaged medicine inspecting unit 300 may include the inflow guide unit 310 that is disposed on an upstream side of the transfer unit 330 to provide a predetermined external force to the bundle of packaged medicines so that the bundle of packaged medicines discharged from the discharge unit 140 of the packaged medicine preparation unit 100 is introduced thereinto to be transferred to the transfer unit 330.

If the inflow guide unit 310 moves the bundle of packaged medicines to the transfer unit 330, the transfer unit 330 moves the bundle of packaged medicines. Thereafter, the photographing unit 350 photographs any packaged medicine of the bundle of packaged medicines and the control unit 200 reads the state of the packaged medicines through the photographed image.

Here, if the photographing unit 350 photographs any packaged medicines of the bundle of packaged medicines, the light source unit 360 may provide the photographing unit 350 with light for photographing.

The light source unit 360 may be, for example, a backlight.

Meanwhile, at least one of the photographing unit 350 and the light source unit 360 may include a polarizing unit that makes polarization be incident on the photographing unit 350 to ensure the accuracy of the image photographed by the photographing unit 350. Here, the polarizing unit may be a kind of polarizing film.

The image photographed by the photographing unit 350 may eliminate the effect of light blur due to the polarization unit, thereby maximizing the accuracy of the medicine inspection.

Meanwhile, the packaged medicine inspecting unit 300 may include an alignment unit (not shown) that may evenly spread medicines within the packaged medicines without the medicines overlapping each other before the packaged medicines are photographed by the photographing unit 350.

Further, the packaged medicine inspecting unit 300 may further include a recognition unit that may be, for example, a barcode scanner capable of recognizing a barcode.

The recognition unit may check what type of medicines and how many medicines are included in the packaged medicines. The control unit 200 receives the information recognized by the recognition unit and then compares the received information with the read result to determine whether the accurate type and number of medicines are packaged in the packing paper.

Figure 10:
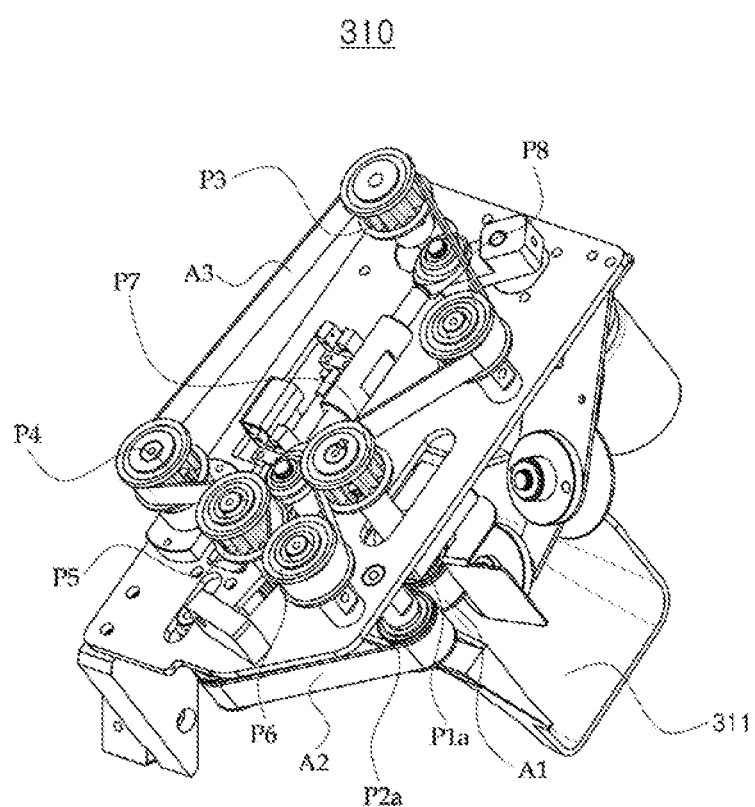
Figure 11:
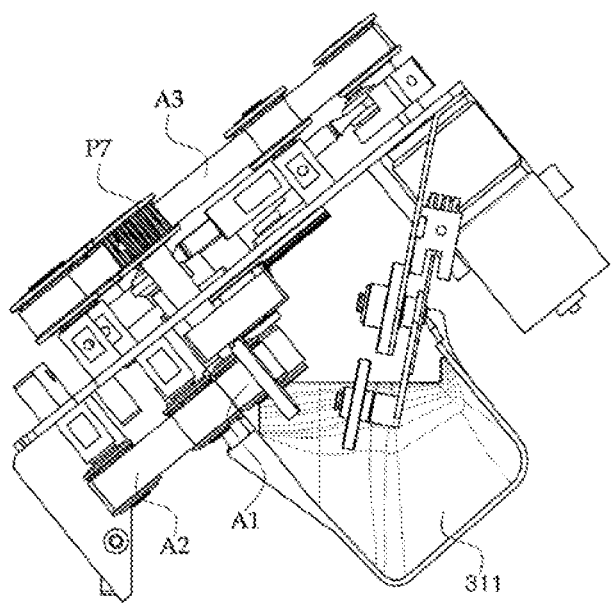
Figure 12:
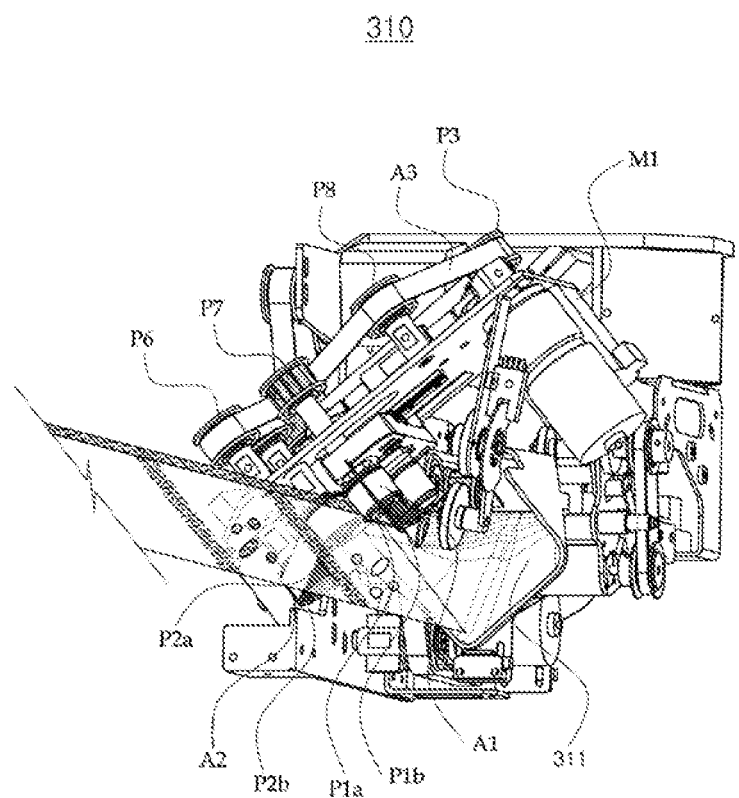

FIGS. 10 to 12 are internal configuration diagrams for explaining an inflow guide unit to the packaged medicine inspecting unit according to the exemplary embodiment of the present disclosure.

Referring to FIGS. 10 to 12, the packaged medicine inspecting unit 300 according to the exemplary embodiment of the present disclosure may include the inflow guide unit 310 that is disposed on the upstream side of the transfer unit 330 to provide the predetermined external force to the bundle of packaged medicines so that the bundle of packaged medicines discharged from the discharge unit 140 of the packaged medicine preparation unit 100 is introduced thereinto to be transferred to the transfer unit 330.

The inflow guide unit 310 allows the bundle of packaged medicines to be introduced in the state in which the bundle of packaged medicines is discharged from the discharge unit 140, and may move the introduced bundle of packaged medicines to the transfer unit 330 in a state different from the state in which the bundle of packaged medicines is discharged.

The inflow guide unit 310 may include a state change means 311 that is formed as a curved surface so that the bundle of packaged medicines discharged in a first state by the discharge unit 140 of the packaged medicine preparation unit 100 moves to the transfer unit 330 in a second state different from the first state.

Here, describing the first state and the second state, the first state may be the state of the bundle of packaged medicines discharged from the discharge unit 140 of the packaged medicine preparation unit 100 and the second state may be the state of the bundle of packaged medicines introduced into the transfer unit 330.

Specifically, the first state may be a state in which the bundle of packaged machines is arranged to be inclined by the arrangement of the discharge unit 140 of the packaged medicine preparation unit 100, and the second state may be a state in which the bundle of packaged medicines arranged to be inclined is disposed horizontally by the state change means 311.

As described above, the inflow guide unit 310 allows the bundle of packaged medicines to be introduced into the transfer unit 330 in the second state, that is, the horizontal state, so that any packaged medicine within the bundle of packaged medicines may be accurately photographed by the photographing unit 350.

Hereinafter, the process of introducing a bundle of packaged medicines into the inflow guide unit 310 will be described.

First, the bundle of packaged medicines discharged from the discharge unit 140 of the packaged medicine preparation unit 100 is introduced between a first inflow conveyor belt A1 and a second inflow conveyor belt A2.

The first inflow conveyor belt A1 may be rotated in an endless track by a rotation of a 1-1-th inflow pulley P1a and a 1-2-th inflow pulley P1b, and the second inflow conveyor belt A2 may be rotated in an endless track by a 2-1-th inflow pulley P2a, a 2-2-th inflow pulley P2b, and a 2-3-th inflow pulley (not shown).

The driving force for the rotation of the inflow pulleys may be provided by an inflow guide driving part M1 which is a kind of motor. Specifically, if the third inflow pulley P3 is rotated by the driving of the inflow guide driving part M1, a fourth inflow pulley P4, a fifth inflow pulley P5, a sixth inflow pulley P6, a seventh inflow pulley P7, and an eighth inflow pulley P8 are rotated by the rotation of a third inflow conveyor belt A3.

If the seventh inflow pulley P7 is rotated, the 1-1-th inflow pulley P1a on the same shaft is rotated, such that the first inflow conveyor belt A1 and the second inflow conveyor belt A2 are rotated in an endless track, thereby moving the bundle of packaged medicines introduced between the first inflow conveyor belt A1 and the second inflow conveyor belt A2 thereinto.

FIGS. 13 to 16 are diagrams for explaining an inspecting process of a bundle of packaged medicines by the packaged medicine inspecting unit according to the exemplary embodiment of the present disclosure.

Figure 13:
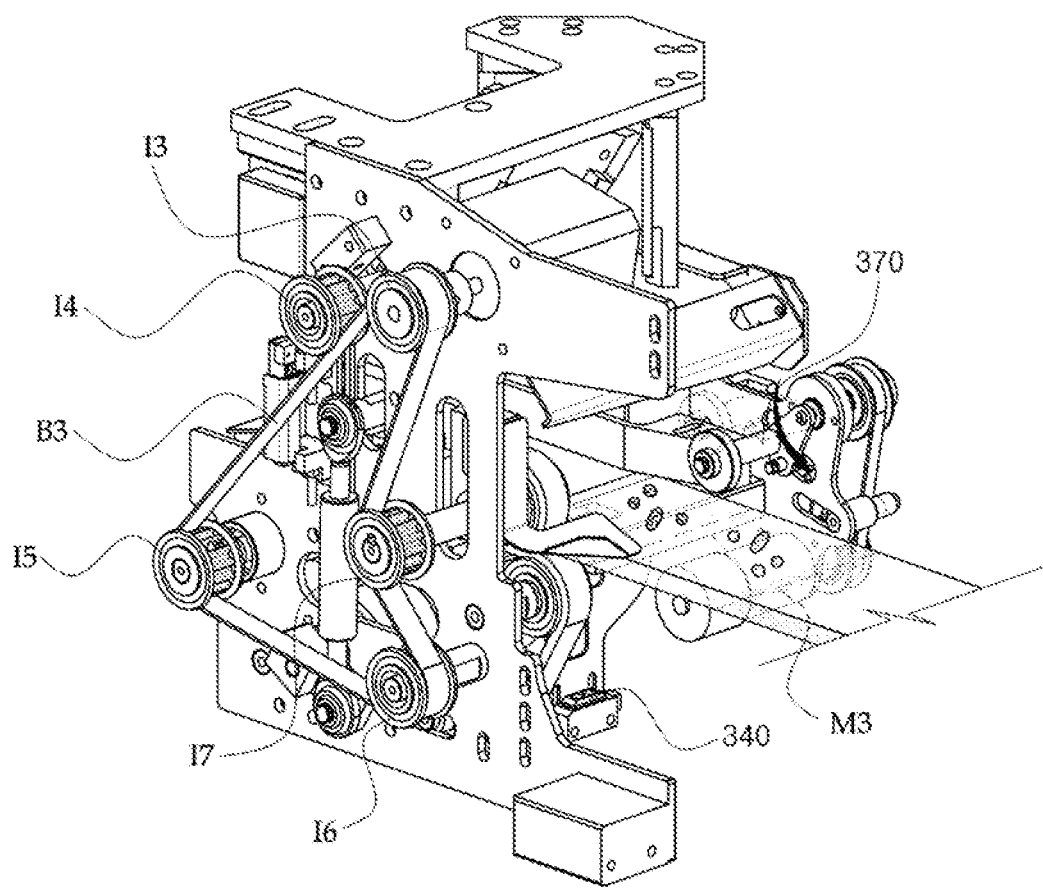
FIGS. 13 to 16 are diagrams for explaining an inspecting process of a bundle of packaged medicines by the packaged medicine inspecting unit according to the exemplary embodiment of the present disclosure.
Figure 14:
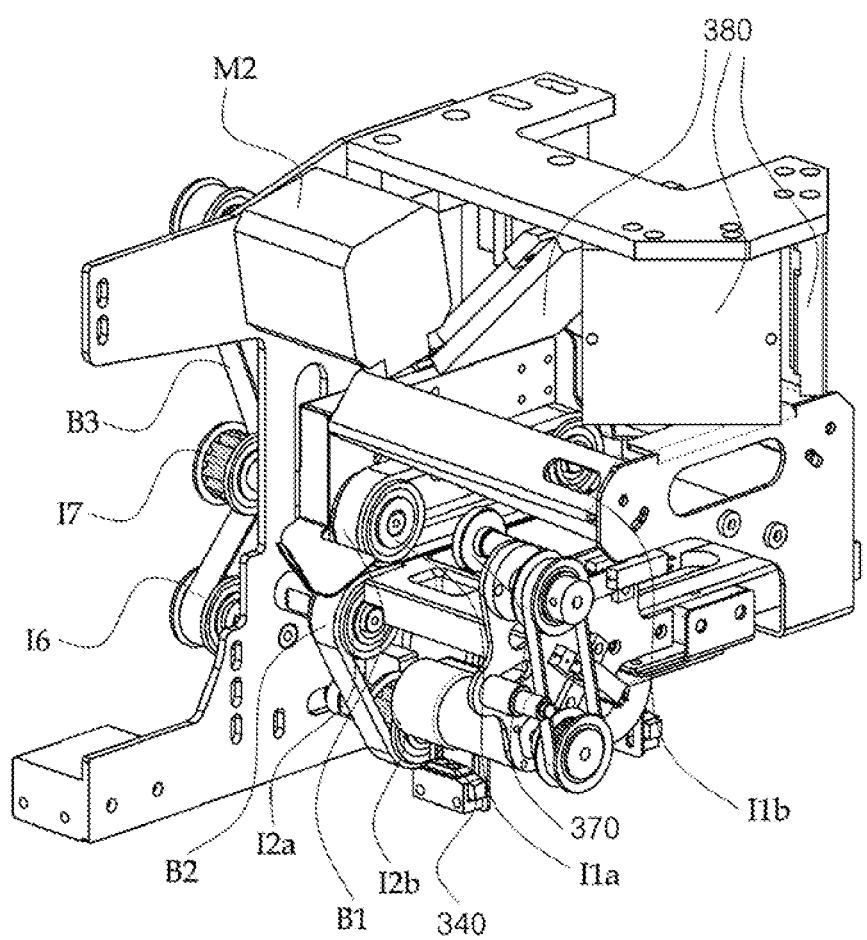

Referring first to FIGS. 13 and 14, if the bundle of packaged medicines moves by the first inflow conveyor belt A1 and the second inflow conveyor belt A2 of the inflow guide unit 310, the bundle of packaged medicines is introduced into the transfer unit 330, that is, between a first inspection conveyor belt B1 and a second inspection conveyor belt B2.

The first inspection conveyor belt B1 may be rotated in an endless track by a rotation of a 1-1-th inspection pulley 11a and a 1-2-th inspection pulley 11b, and the second inspection conveyor belt B2 may be rotated in an endless track by a 2-1-th inspection pulley 12a, a 2-2-th inspection pulley 12b, and a 2-3-th inspection pulley (not shown), and a 2-4-th inspection pulley (not shown).

The driving force for the rotation of the inspection pulleys may be provided by an inspection driving unit M2 which is a kind of motor. Specifically, the third inspection pulley 13 is rotated by the driving of the inspection driving unit M2 and a fourth inspection pulley 14, a fifth inspection pulley 15, a sixth inspection pulley 16, and a seventh inspection pulley 17 are rotated by the rotation of a third inspection conveyor belt B3.

If the seventh inspection pulley 17 is rotated, the 1-1-th inspection pulley 11a on the same shaft is rotated, such that the first inspection conveyor belt B1 and the second inspection conveyor belt B2 are rotated in an endless track, thereby moving the bundle of packaged medicines introduced between the first inspection conveyor belt B1 and the second inspection conveyor belt B2 thereinto.

Meanwhile, the bundle of packaged medicines introduced between the first inspection conveyor belt B1 and the second inspection conveyor belt B2 may be detected by a third detection unit 340.

The third detection unit 340 is one component of the packaged medicine inspecting unit 300 and may be a kind of sensor sensing whether the bundle of packaged medicines introduced thereinto by the inflow guide unit 310 is introduced into the transfer unit 330, that is, between the first inspection conveyor belt B1 and the second inspection conveyor belt B2, for example, an optical sensor.

However, the third detection unit 340 is not limited to the optical sensor, and may be an ultrasonic sensor, a tact switch or the like.

When the bundle of packaged medicines is introduced between the first inspection conveyor belt B1 and the second inspection conveyor belt B2 and is detected by the third detection unit 340, the control unit 200 rotates a first tension providing unit 370 by a driving force of a tension providing motor M3, such that the bundle of packaged medicines moves while maintaining a predetermined tension.

Figure 15:
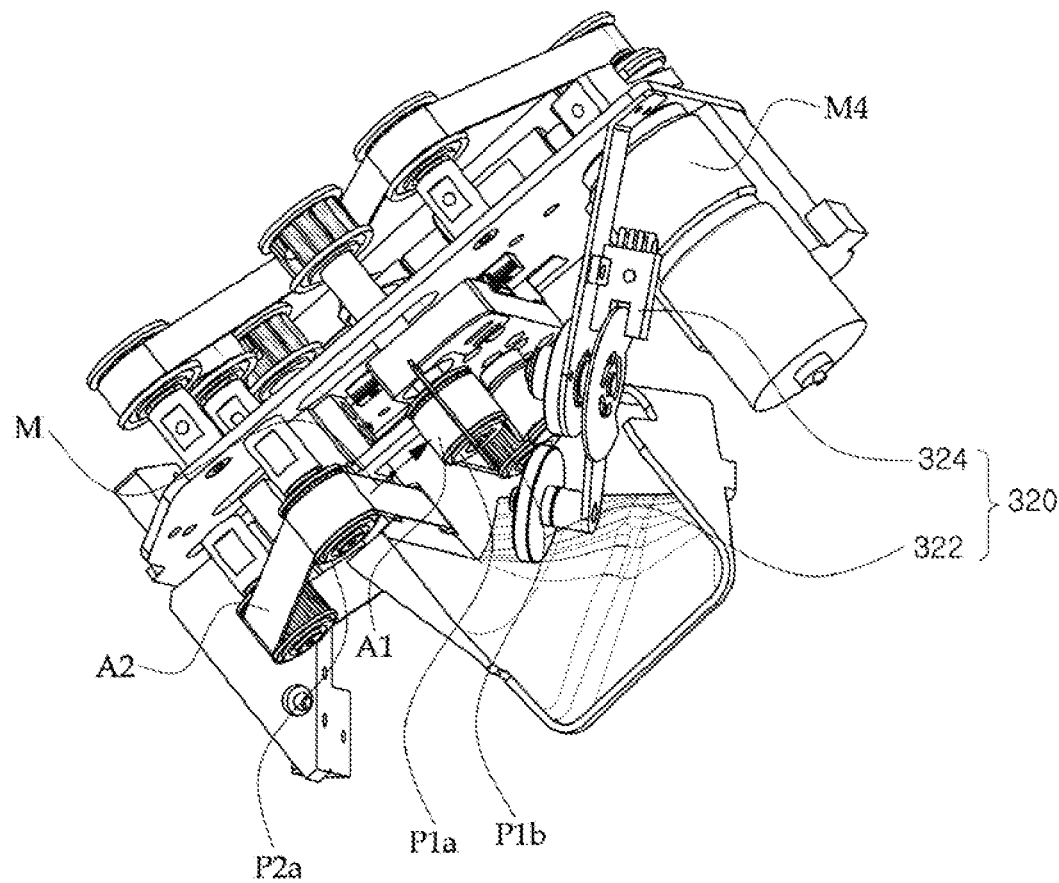

Meanwhile, if the bundle of packaged medicines introduced between the first inspection conveyor belt B1 and the second inspection conveyor belt B2 is detected by the third detection unit 340, the inflow guide unit 310 may be in the state shown in FIG. 15 by the control unit 200.

Referring to FIG. 15, a position of at least one of the first inflow conveyor belt A1 and the second inflow conveyor belt A2 moves by the control unit 200 and thus the predetermined external force applied to the bundle of packaged medicines may be reduced.

Specifically, if the third detection unit 340 senses that the bundle of packaged medicines is introduced between the first inspection conveyor belt B1 and the second inspection conveyor belt B2, the control unit 200 drives a driving motor M4 to move positions of the 1-1-th and 1-2-th inflow pulleys P1a and P1b so that the 1-1-th and 1-2-th inflow pulleys P1a and P1b are spaced apart from the 2-1-th inflow pulley P2a and the 2-2-th inflow pulley P2b.

As a result, the first inflow conveyor belt A1 is spaced apart from the second inflow conveyor belt A2, and the predetermined external force applied to the bundle of packaged medicines is reduced.

In this case, the bundle of packaged medicines introduced into the inflow guide unit 310 may be contacted by the second detection unit 320, such that the bundle of packaged medicines is continuously introduced horizontally into the transfer unit 330.

The second detection unit 320 may be a component that senses the degree of the tension while maintaining the tension of the bundle of packaged machines moving to the transfer unit 330.

The second detection unit 320 may include a second tension providing unit 322 for providing a tension to the bundle of packaged medicines and a position detection unit 324 that is a kind of sensor sensing the position of the second tension providing unit 322.

The position detection unit 324 may be the optical sensor, the ultrasonic sensor, the tact switch or the like, and may sense the position of the second tension providing unit 322 to provide a signal to the control unit 200. This will be described below.

Figure 16:
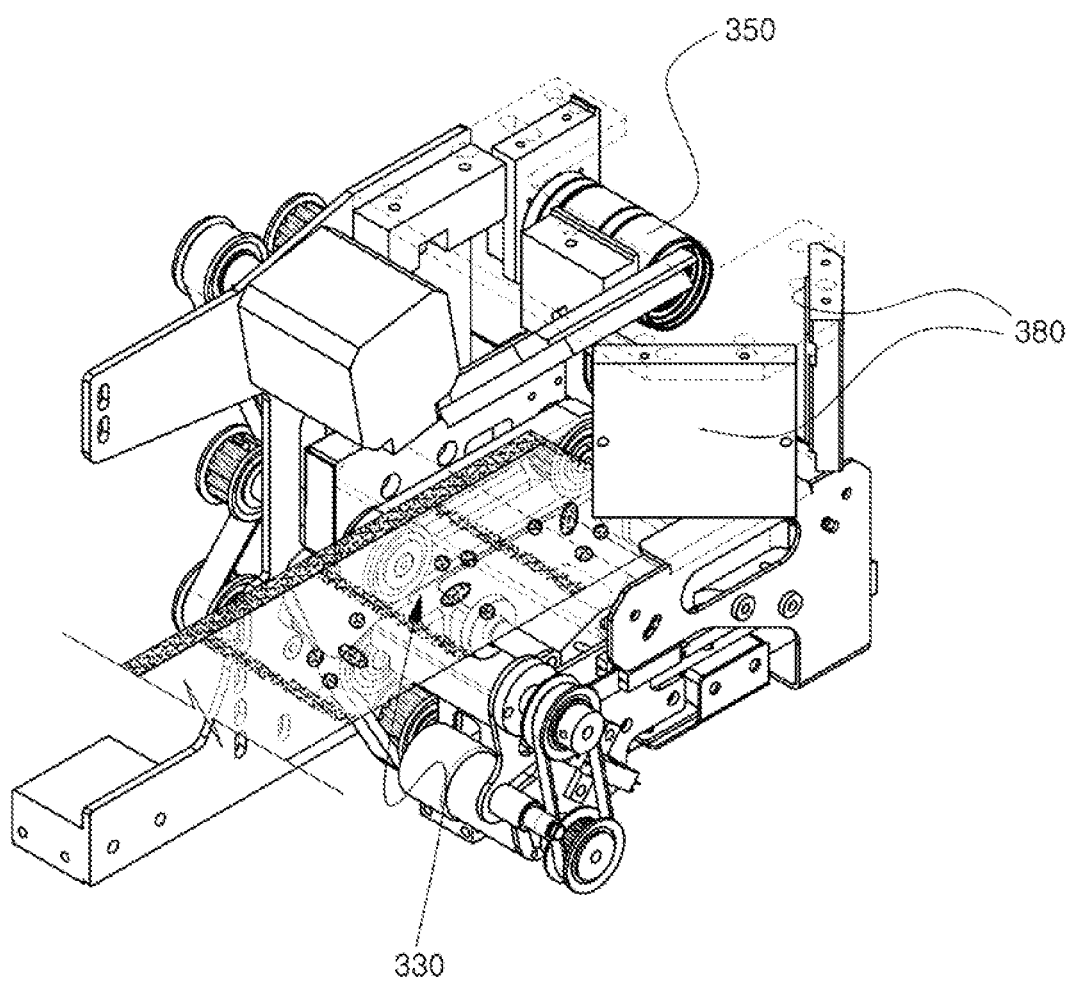

Referring to FIG. 16, if the bundle of packaged medicines moves by the transfer unit 330, any packaged medicines within the bundle of packaged medicines are photographed by the photographing unit 350. At this time, the light of the light source unit 360 may be used.

The light irradiated from the light source unit 360 may be reflected by at least one reflector 380 and may be incident on the photographing unit 350.

The control unit 200 reads the state of any packaged medicine using the image photographed by the photographing unit 350.

Here, at least one of the photographing unit 350 and the light source unit 360 may include the polarizing unit that makes polarization be incident on the photographing unit 350 to ensure the accuracy of the image photographed by the photographing unit 350. Here, the polarizing unit may be polarizing film, for example.

The polarizing unit may prevent the phenomena such as the light blur from occurring in the photographed image.

4. Control Process of Control Apparatus

As described above, the control apparatus 1 according to the exemplary embodiment of the present disclosure may include the packaged medicine preparation unit 100, the post-processing unit 300, and the control unit 200.

The post-processing unit 300 may be an apparatus that may be detachably connected to the packaged medicine preparation unit 100, but is not necessarily limited thereto, and may also be an apparatus that is disposed to be spaced apart from the packaged medicine preparation unit 100.

The packaged medicine preparation unit 100 may include the discharge unit 140 that moves the position of the bundle of packaged medicines prepared by one capsule in a single dose to perform the post-process thereon and the post-processing unit 300 may include the transfer unit 330 that moves the bundle of packaged medicines to perform the post-process thereon if the bundle of packaged medicines discharged from the discharge unit 140 is introduced thereinto.

Here, the control apparatus 1 according to the exemplary embodiment of the present disclosure allows a bundle of packaged medicines in which a large amount of medicines are packaged by one capsule in a single dose to be smoothly transferred to the post-process for a specific purpose, thereby preventing the bundle of packaged medicines from being cut abnormally. For this, the control unit 200 may allow the transfer speed of the bundle of packaged medicines by the transfer unit 330 to be associated with the discharge speed of the bundle of packaged medicines by the discharge unit 140 and control at least one of the transfer unit 330 and the discharge unit 140 to allow the post-processing unit 300 to perform the post-process thereon without damaging the bundle of packaged medicines.

The control unit 200 may acquire at least one of first information associated with the discharge speed of the bundle of packaged medicines by the discharge unit 140 and second information associated with the transfer speed of the bundle of packaged medicines by the transfer unit 330 and control at least one of the transfer unit 330 and the discharge unit 140 based on the acquired information.

For example, the control unit 200 acquires the first information associated with the discharge speed of the bundle of packaged medicines by the discharge unit 140 and controls the transfer unit 330 based on the acquired first information so that the transfer unit 330 may control the transfer speed of the bundle of packaged medicines.

In other words, the control unit 200 may synchronize the transfer speed of the bundle of packaged medicines by the transfer unit 330 with the discharge speed of the bundle of packaged medicines by the discharge unit 140 based on the first information.

Here, the synchronization may mean by way of example that the speed is equal.

Meanwhile, if the control unit 200 acquires third information associated with the bundle of packaged medicines existing between the transfer unit 330 and the discharge unit 140 while controlling at least one of the transfer unit 330 and the discharge unit 140 by the foregoing method, the control unit 200 may control the transfer unit 330 based on the acquired third information so that the transfer unit 330 may control the transfer speed of the bundle of packaged medicines.

For example, the control unit 200 may stop the transfer unit 330 or reduce the speed of the transfer unit 330 based on the acquired third information.

Further, if the control unit 300 stops the transfer unit 330 based on the third information and then stops acquiring the third information, the control unit 200 may control the transfer unit 330 so that the transfer unit 330 transfers the bundle of packaged medicines again.

Alternatively, if the control unit 300 reduces the speed of the transfer unit 330 based on the third information and then stops acquiring the third information, the control unit 200 may control the transfer unit 330 so that the transfer speed of the bundle of packaged medicines by the transfer unit 330 returns to the original speed.

Hereinafter, the case where the post-processing unit 300 is the packaged medicine inspecting unit 300 inspecting whether or not any packaged medicine of the bundle of packaged medicines introduced thereinto corresponds to the medicine dispensing request will be described in detail.

The control unit 200 may acquire the first information associated with the discharge speed of the bundle of packaged medicines by the discharge unit 140 to control the transfer speed of the bundle of packaged medicines by the transfer unit 330. The first information may be provided by the first detection unit 150 of the packaged medicine preparation unit 100.

That is, the control unit 200 may acquire the detected result by the first detection unit 150 to control the transfer unit 330 so that the transfer unit 330 may control the transfer speed of the bundle of packaged medicines.

The control unit 200 may acquire the detected result by the first detection unit 150 so that the transfer speed of the bundle of packaged medicines by the transfer unit is synchronized with the discharge speed of the bundle of packaged medicines by the discharge unit 140. For example, the control unit may control the transfer unit 330 to make the transfer speed be equal to the discharge speed.

As a result, the bundle of packaged medicines is smoothly transferred from the packaged medicine preparation unit 100 to the packaged medicine inspecting unit 300 without being cut.

On the other hand, the discharge speed of the bundle of packaged medicines by the discharge unit 140 of the packaged medicine preparation unit 100 may be constant, but may vary from time to time in some cases.

Even in the case, the control unit 200 synchronizes the transfer speed of the bundle of packaged medicines by the transfer unit 330 with the varying discharge speed of the bundle of packaged medicines by the discharge unit 140, thereby smoothly transferring the bundle of packaged medicines.

Meanwhile, if the control unit 200 acquires the third information associated with the bundle of packaged medicines existing between the transfer unit 330 and the discharge unit 330 while controlling the transfer speed of the bundle of packaged medicines by the transfer unit based on the detected result by the first detection unit 150, the control unit 200 may control the transfer unit 330 so that the transfer unit 330 may control the transfer speed of the bundle of packaged medicines based on the acquired third information.

The third information may be the result detected by the second detection unit 320 of the packaged medicine inspecting unit 300 and the second detection unit 320 may be a component for detecting whether the bundle of packaged medicines existing between the transfer unit 330 and the discharge unit 140 exists in a predetermined space between the transfer unit 330 and the discharge unit 140.

The second detection unit 320 may be a component for detecting the degree of the tension while maintaining the tension of the bundle of packaged medicines moving to the transfer unit 330 and may include the second tension providing unit 322 for providing a tension to the bundle of packaged medicines and the position detection unit 324 that is a kind of sensor detecting the position of the second tension providing unit 322.

If the tension of the bundle of packaged medicines existing between the transfer unit 330 and the discharge unit 140 becomes too strong, the bundle of packaged medicines moves upward, such that the second tension providing unit 322 is rotated and the position detection unit 324 detects the rotation.

In this case, if the bundle of packaged medicines continuously moves by the transfer unit 330, there is a possibility that the bundle of packaged medicines will be cut off. Therefore, if the detected result by the second detection unit 320 is acquired, the control unit 200 may control the transfer unit 330 so that the transfer unit 330 may control the transfer speed of the bundle of packaged medicines. For example, the control unit 200 may stop the transfer unit 330 or reduce the speed of the transfer unit 330.

Further, if the transfer unit 330 stops and then the information acquired from the second detection unit 320 is lost, the control unit 300 may control the transfer unit 330 so that the transfer unit 330 transfers the bundle of packaged medicines.

Alternatively, if the speed of the transfer unit 330 is reduced and then the information acquired from the second detection unit 320 is lost, the control unit 200 may control the transfer unit 330 so that the transfer speed of the bundle of packaged medicines by the transfer unit 330 returns to the original speed. Meanwhile, the second detection unit may be an optical sensor including a light emitting element for emitting light and a light receiving element for receiving the light.

In this case, the second detection unit may detect whether the bundle of packaged medicines exists in the predetermined space between the transfer unit 330 and the discharge unit 140 based on the change in light irradiated from the light emitting element to the light receiving element due to the bundle of packaged medicines existing between the transfer unit 330 and the discharge unit 140.

For example, if the light irradiated from the light emitting element to the light receiving element is blocked by the bundle of packaged medicines, the control unit 200 may determine that the bundle of packaged medicines exists in the predetermined space, or vice versa.

Meanwhile, the control unit 200 may be mounted on the packaged medicine preparation unit 100 or may be mounted on the post-processing unit 300, but the mounting location of the control unit 200 is not necessarily limited thereto. Therefore, the control unit 200 may be a separate component from the packaged medicine preparation unit 100 and the post-processing unit 300.

While exemplary embodiments have been shown and described above, it will be apparent to those skilled in the art that modifications and variations could be made without departing from the spirit and scope of the present disclosure as defined by the appended claims.

For example, the pulley that rotates the first inflow conveyor belt A1, the second inflow conveyor belt A2, the first inspection conveyor belt B1 and the second inspection conveyor belt B2 for moving the position of the bundle of packaged medicines is not necessarily limited to those described above, and the number or positions of pulleys, and the like may be freely changed by those skilled in the art.

In addition, a means for rotating the first inflow conveyor belt A1, the second inflow conveyor belt A2, the first inspection conveyor belt B1 and the second inspection conveyor belt B2 is not limited to the pulley.

What is claimed is:
1. A control apparatus, comprising:
a packaged medicine preparation unit discharging a bundle of packaged medicines in which a large amount of medicines are prepared by one capsule in a single dose to perform a post-process on the bundle of packaged medicines for a specific purpose based on a medicine dispensing request; and
a post-processing unit introduced with the bundle of packaged medicines discharged from the packaged medicine preparation unit to perform the post-process thereon,
wherein the packaged medicine preparation unit includes:
a discharge unit moving a position of the bundle of packaged medicines prepared by one capsule in the single dose to perform the post-process thereon, and
the post-processing unit includes
a transfer unit moving the position of the bundle of packaged medicines to perform the post-process thereon if the bundle of packaged medicines discharged from the discharge unit is introduced thereinto,
wherein the control apparatus includes a control unit allowing a transfer speed of the bundle of packaged medicines by the transfer unit to be associated with a discharge speed of the bundle of packaged medicines by the discharge unit and controlling at least one of the transfer unit and the discharge unit to allow the post-processing unit to perform the post-process thereon without damaging the bundle of packaged medicines,
wherein the post-processing unit further includes a packaged medicine inspecting unit inspecting whether or not any packaged medicine of the bundle of packaged medicines introduced thereinto corresponds to the medicine dispensing request,
wherein the packaged medicine preparation unit further includes a first detection unit for acquiring the discharge speed of the bundle of packaged medicines by the discharge unit, and the control unit acquires a detected result by the first detection unit to control the transfer unit so that the transfer unit controls the transfer speed of the bundle of packaged medicines, wherein the packaged medicine inspecting unit includes a second detection unit detecting whether the bundle of packaged medicines existing between the transfer unit and the discharge unit exists in a predetermined space between the transfer unit and the discharge unit, wherein the control unit controls at least one of the transfer unit and the discharge unit and controls the transfer unit so that the transfer unit controls the transfer speed of the bundle of packaged medicines if a detected result by the second detection unit is acquired, wherein the control unit stops the transfer unit if the detected result by the second detection unit is acquired, and wherein, if the transfer unit stops and then the information acquired from the second detection unit is lost, the control unit controls the transfer unit so that the transfer unit transfers the bundle of packaged medicines.

2. The control apparatus as claimed in claim 1, wherein the control unit acquires at least one of first information associated with the discharge speed of the bundle of packaged medicines by the discharge unit and second information associated with the transfer speed of the bundle of packaged medicines by the transfer unit and controls at least one of the transfer unit and the discharge unit based on the acquired information.

3. The control apparatus as claimed in claim 1, wherein the control unit acquires first information associated with the discharge speed of the bundle of packaged medicines by the discharge unit and controls the transfer unit based on the acquired first information so that the transfer unit controls the transfer speed of the bundle of packaged medicines.

4. The control apparatus as claimed in claim 1, wherein the control unit acquires first information associated with the discharge speed of the bundle of packaged medicines by the discharge unit and controls the transfer unit based on the acquired first information so that the transfer speed of the bundle of packaged medicines by the transfer unit is synchronized with the discharge speed of the bundle of packaged medicines by the discharge unit.

5. The control apparatus as claimed in claim 1, wherein the control unit acquires first information associated with the discharge speed of the bundle of packaged medicines by the discharge unit and controls the transfer unit based on the acquired first information so that the transfer speed of the bundle of packaged medicines by the transfer unit is equal to the discharge speed of the bundle of packaged medicines by the discharge unit.

6. The control apparatus as claimed in claim 1, wherein if the control unit controls at least one of the transfer unit and the discharge unit and acquires third information associated with the bundle of packaged medicines existing between the transfer unit and the discharge unit, the control unit controls the transfer unit based on the acquired third information so that the transfer unit controls the transfer speed of the bundle of packaged medicines.

7. The control apparatus as claimed in claim 6, wherein the control unit stops the transfer unit based on the acquired third information.

8. The control apparatus as claimed in claim 7, wherein if the control unit stops the transfer unit and then stops acquiring the third information, the control unit controls the transfer unit so that the transfer unit transfers the bundle of packaged medicines.

9. The control apparatus as claimed in claim 1, wherein the packaged medicine inspecting unit includes an inflow guide unit that is disposed on an upstream side of the transfer unit to provide a predetermined external force to the bundle of packaged medicines so that the bundle of packaged medicines discharged from the discharge unit is introduced thereinto to be transferred to the transfer unit.

10. The control apparatus as claimed in claim 9, wherein the inflow guide unit includes a state change means that is formed as a curved surface so that the bundle of packaged medicines discharged in a first state by the discharge unit moves to the transfer unit in a second state different from the first state.

11. The control apparatus as claimed in claim 9, wherein the inflow guide unit allows the bundle of packaged medicines to be introduced in the state in which the bundle of packaged medicines is discharged from the discharge unit, and transfers the introduced bundle of packaged medicines to the transfer unit in a state different from the state in which the bundle of packaged medicines is discharged.

12. The control apparatus as claimed in claim 9, wherein the packaged medicine inspecting unit further includes a third detection unit detecting whether the bundle of packaged medicines introduced thereinto by the inflow guide unit is introduced into the transfer unit, and
the control unit controls the inflow guide unit to reduce the predetermined external force if a detected result by the third detection unit is acquired.

13. The control apparatus as claimed in claim 12, wherein the inflow guide unit includes a first inflow conveyor belt and a second inflow conveyor belt each contacting an upper surface and a lower surface of the bundle of packaged medicines, and
the control unit moves a position of at least one of the first inflow conveyor belt and the second inflow conveyor belt to reduce the predetermined external force if the detected result by the third detection unit is acquired.

14. The control apparatus as claimed in claim 12, wherein the packaged medicine inspecting unit further includes a tension maintaining means pressing the bundle of packaged medicines to maintain a tension of the bundle of packaged medicines introduced into the transfer unit if the bundle of packaged medicines introduced thereinto by the inflow guide unit is introduced into the transfer unit.

* * * * *